US007798992B2

United States Patent
Ortiz (10) Patent No.: US 7,798,992 B2
(45) Date of Patent: Sep. 21, 2010

(54) LUMEN TRAVERSING DEVICE (75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1356 days.

(21) Appl. No.: 11/267,463

(22) Filed: Nov. 4, 2005

(65) Prior Publication Data
US 2007/0106302 A1 May 10, 2007

(51) Int. Cl.
*A61M 31/00* (2006.01)
(52) U.S. Cl. ............... 604/95.01; 604/106; 606/108
(58) Field of Classification Search .......... 606/108, 606/191, 200, 198; 604/101.01, 95.01, 95.03, 604/104–109, 101.03, 528; 600/115, 116, 600/139, 141
See application file for complete search history.

(56) References Cited

U.S. PATENT DOCUMENTS

| 2,004,013 A | | 6/1935 | Reed |
| 2,004,014 A | | 6/1935 | Sanford |
| 2,004,172 A | | 6/1935 | Niday |
| 4,176,662 A | * | 12/1979 | Frazer ..................... 600/114 |
| 4,389,208 A | * | 6/1983 | LeVeen et al. ........... 604/95.03 |
| 4,838,859 A | * | 6/1989 | Strassmann ............ 604/95.03 |
| 4,841,888 A | | 6/1989 | Mills et al. |
| 4,848,168 A | * | 7/1989 | Negishi .................... 73/865.8 |
| 4,921,484 A | * | 5/1990 | Hillstead ................. 604/104 |
| 4,934,786 A | * | 6/1990 | Krauter .................... 385/118 |
| 5,041,129 A | | 8/1991 | Hayhurst et al. |
| 5,080,663 A | | 1/1992 | Mills et al. |
| 5,090,259 A | * | 2/1992 | Shishido et al. ........... 73/866.5 |
| 5,144,848 A | * | 9/1992 | Uenishi et al. ........... 73/866.5 |
| 5,197,971 A | * | 3/1993 | Bonutti ..................... 606/192 |
| 5,217,486 A | | 6/1993 | Rice et al. |
| 5,269,809 A | | 12/1993 | Hayhurst et al. |
| 5,376,101 A | | 12/1994 | Green et al. |
| 5,398,670 A | * | 3/1995 | Ortiz et al. ................. 600/114 |
| 5,437,681 A | | 8/1995 | Meade et al. |
| 5,462,558 A | | 10/1995 | Kolesa et al. |
| 5,514,159 A | | 5/1996 | Matula et al. |
| 5,540,705 A | | 7/1996 | Meade et al. |
| 5,571,119 A | | 11/1996 | Atala |
| 5,584,861 A | | 12/1996 | Swain et al. |
| 5,662,587 A | * | 9/1997 | Grundfest et al. ........... 600/114 |
| 5,709,693 A | | 1/1998 | Taylor |
| 5,713,910 A | | 2/1998 | Gordon et al. |
| 5,755,730 A | | 5/1998 | Swain et al. |

(Continued)

FOREIGN PATENT DOCUMENTS

DE  44 29 117 A1  2/1996

(Continued)

*Primary Examiner*—Todd E Manahan
*Assistant Examiner*—Erin Colello
(74) *Attorney, Agent, or Firm*—Nutter McClennen & Fish LLP (57) ABSTRACT

Various exemplary methods and devices are provided for traversing a lumen, such as the gastrointestinal tract. The devices can include an elongate body having distally positioned tubing elements and proximally positioned control elements. The tubing elements are adapted for selective and independent radial expansion and contraction and longitudinal movement, such that movement of the tubing elements can drive the device through a lumen. In addition, the tubing elements can include a traction surface to reduce slippage.

15 Claims, 9 Drawing Sheets

U.S. PATENT DOCUMENTS

| | | | |
|---|---|---|---|
| 5,814,071 A | | 9/1998 | McDevitt et al. |
| 5,827,304 A * | | 10/1998 | Hart .......................... 606/159 |
| 5,860,992 A | | 1/1999 | Daniel et al. |
| 5,868,708 A * | | 2/1999 | Hart et al. .................. 604/104 |
| 5,887,594 A | | 3/1999 | LoCicero, III |
| 5,899,921 A | | 5/1999 | Caspari et al. |
| 5,902,321 A | | 5/1999 | Caspari et al. |
| 5,906,591 A * | | 5/1999 | Dario et al. ............... 604/95.03 |
| 6,007,482 A * | | 12/1999 | Madni et al. ................ 600/115 |
| 6,010,515 A | | 1/2000 | Swain et al. |
| 6,036,694 A | | 3/2000 | Goble et al. |
| 6,162,171 A * | | 12/2000 | Ng et al. .................... 600/141 |
| 6,200,329 B1 | | 3/2001 | Fung et al. |
| 6,249,076 B1 | | 6/2001 | Madden et al. |
| 6,346,111 B1 | | 2/2002 | Gordon et al. |
| 6,358,259 B1 | | 3/2002 | Swain et al. |
| 6,443,962 B1 | | 9/2002 | Gaber |
| 6,454,778 B2 | | 9/2002 | Kortenbach |
| 6,494,888 B1 | | 12/2002 | Laufer et al. |
| 6,500,195 B2 | | 12/2002 | Bonutti |
| 6,506,196 B1 | | 1/2003 | Laufer |
| 6,524,328 B2 | | 2/2003 | Levinson |
| 6,540,789 B1 | | 4/2003 | Silverman et al. |
| 6,558,400 B2 | | 5/2003 | Deem et al. |
| 6,572,629 B2 | | 6/2003 | Kalloo et al. |
| 6,616,678 B2 * | | 9/2003 | Nishtala et al. ............. 606/198 |
| 6,626,861 B1 | | 9/2003 | Hart et al. |
| 6,648,814 B2 * | | 11/2003 | Kim et al. .................... 600/114 |
| 6,663,639 B1 | | 12/2003 | Laufer et al. |
| 6,719,763 B2 | | 4/2004 | Chung et al. |
| 6,746,460 B2 | | 6/2004 | Gannoe et al. |
| 6,755,843 B2 | | 6/2004 | Chung et al. |
| 6,764,441 B2 * | | 7/2004 | Chiel et al. .................. 600/115 |
| 6,773,440 B2 | | 8/2004 | Gannoe et al. |
| 6,773,441 B1 | | 8/2004 | Laufer et al. |
| 6,821,858 B2 | | 11/2004 | Namatame et al. |
| 6,824,508 B2 * | | 11/2004 | Kim et al. .................... 600/101 |
| 6,835,200 B2 | | 12/2004 | Laufer et al. |
| 6,869,395 B2 | | 3/2005 | Page et al. |
| 6,908,427 B2 | | 6/2005 | Fleener et al. |
| 6,955,643 B2 | | 10/2005 | Gellman et al. |
| 6,988,986 B2 * | | 1/2006 | Gross .......................... 600/114 |
| 7,044,245 B2 * | | 5/2006 | Anhalt et al. ................ 180/9.1 |
| 7,090,688 B2 * | | 8/2006 | Nishtala et al. ............. 606/198 |
| 7,218,035 B2 * | | 5/2007 | Khajepour et al. .......... 310/328 |
| 7,635,345 B2 * | | 12/2009 | Gross et al. ............. 604/99.01 |
| 7,635,346 B2 * | | 12/2009 | Cabiri et al. ............. 604/99.01 |
| 2001/0023352 A1 | | 9/2001 | Gordon et al. |
| 2002/0107530 A1 | | 8/2002 | Sauer et al. |
| 2002/0193809 A1 | | 12/2002 | Meade et al. |
| 2003/0032967 A1 | | 2/2003 | Park et al. |
| 2003/0083674 A1 | | 5/2003 | Gibbens |
| 2003/0109900 A1 | | 6/2003 | Martinek |
| 2003/0120265 A1 | | 6/2003 | Deem et al. |
| 2003/0120292 A1 | | 6/2003 | Park et al. |
| 2003/0171760 A1 | | 9/2003 | Gambale |
| 2003/0181924 A1 | | 9/2003 | Yamamoto et al. |
| 2003/0225312 A1 | | 12/2003 | Suzuki et al. |
| 2003/0229296 A1 | | 12/2003 | Ishikawa et al. |
| 2003/0229332 A1 | | 12/2003 | Intoccia |
| 2003/0233104 A1 | | 12/2003 | Gellman et al. |
| 2003/0233108 A1 | | 12/2003 | Gellman et al. |
| 2003/0236531 A1 | | 12/2003 | Couvillon |
| 2004/0002720 A1 | | 1/2004 | Kortenbach et al. |
| 2004/0006351 A1 | | 1/2004 | Gannoe et al. |
| 2004/0024386 A1 | | 2/2004 | Deem et al. |
| 2004/0034369 A1 | | 2/2004 | Sauer et al. |
| 2004/0059350 A1 | | 3/2004 | Gordon et al. |
| 2004/0082963 A1 | | 4/2004 | Gannoe et al. |
| 2004/0098050 A1 | | 5/2004 | Foerster et al. |
| 2004/0102681 A1 * | | 5/2004 | Gross .......................... 600/116 |
| 2004/0122452 A1 | | 6/2004 | Deem et al. |
| 2004/0122453 A1 | | 6/2004 | Deem et al. |
| 2004/0122473 A1 | | 6/2004 | Ewers et al. |
| 2004/0147958 A1 | | 7/2004 | Lam et al. |
| 2004/0158143 A1 | | 8/2004 | Flaherty et al. |
| 2004/0162568 A1 | | 8/2004 | Saadat et al. |
| 2004/0167546 A1 | | 8/2004 | Saadat et al. |
| 2004/0186349 A1 * | | 9/2004 | Ewers et al. ................ 600/114 |
| 2004/0193184 A1 | | 9/2004 | Laufer et al. |
| 2004/0194790 A1 | | 10/2004 | Laufer et al. |
| 2004/0210243 A1 | | 10/2004 | Gannoe et al. |
| 2004/0215058 A1 | | 10/2004 | Zirps et al. |
| 2005/0015101 A1 | | 1/2005 | Gibbens et al. |
| 2005/0033319 A1 | | 2/2005 | Gambale et al. |
| 2005/0038335 A1 * | | 2/2005 | Gross et al. ................. 600/407 |
| 2005/0055038 A1 | | 3/2005 | Kelleher et al. |
| 2005/0070921 A1 | | 3/2005 | Ortiz et al. |
| 2005/0070926 A1 | | 3/2005 | Ortiz |
| 2005/0070931 A1 | | 3/2005 | Li et al. |
| 2005/0070934 A1 | | 3/2005 | Tanaka et al. |
| 2005/0070935 A1 | | 3/2005 | Ortiz |
| 2005/0075653 A1 | | 4/2005 | Saadat et al. |
| 2005/0075654 A1 | | 4/2005 | Kelleher |
| 2005/0113892 A1 | | 5/2005 | Sproul |
| 2005/0124856 A1 * | | 6/2005 | Fujikura et al. ............. 600/115 |
| 2005/0143760 A1 | | 6/2005 | Imran |
| 2005/0143762 A1 | | 6/2005 | Paraschac et al. |
| 2005/0149067 A1 | | 7/2005 | Takemoto et al. |
| 2005/0165419 A1 | | 7/2005 | Sauer et al. |
| 2005/0192599 A1 | | 9/2005 | Demarais |
| 2005/0192601 A1 | | 9/2005 | Demarais |
| 2005/0197531 A1 * | | 9/2005 | Cabiri et al. ................ 600/116 |
| 2005/0203488 A1 | | 9/2005 | Michlitsch et al. |
| 2005/0215855 A1 * | | 9/2005 | Machida .................... 600/114 |
| 2005/0222496 A1 * | | 10/2005 | Sekiguchi ................... 600/115 |
| 2008/0091068 A1 * | | 4/2008 | Terliuc ....................... 600/116 |

FOREIGN PATENT DOCUMENTS

| | | |
|---|---|---|
| GB | 2 020 557 A | 11/1979 |
| WO | WO-95/19140 | 7/1995 |
| WO | WO-00/61012 | 10/2000 |
| WO | WO-01/10312 | 2/2001 |
| WO | WO-01/66001 | 9/2001 |
| WO | WO-01/89393 | 11/2001 |
| WO | WO-02/096327 | 12/2002 |
| WO | WO-2004/021894 | 3/2004 |
| WO | WO-2005/034729 | 4/2005 |
| WO | WO 2005074377 A2 * | 8/2005 |

* cited by examiner

LUMEN TRAVERSING DEVICE

BACKGROUND OF THE INVENTION

A variety of medical devices are passed through a lumen of a tubular body part for surgical, diagnostic and/or delivery purposes. An endoscope, for example, is an instrument that is used for visually examining and/or facilitating treatment of a site at an internal body cavity, such as in the gastrointestinal (GI) tract. During a procedure involving use of an endoscope, the instrument must be carefully navigated through the lumen to access the desired site and to avoid perforating the intraluminal wall of the body part.

However, many conventional endoscopes have an inherent problem of access during intraluminal work in the gastrointestinal tract. Endoscopes are limited in their access since pushing a flexible scope around bends in the GI tract becomes increasingly difficult as the length of the lumen increases. Other devices, such as balloon-based bowel crawlers, have limits to their successful use due to issues of speed and traction on the internal bowel wall. That is, it can prove difficult to use the bowel wall to push/pull the device given the need to avoid tearing the gastrointestinal tract and the variations in lumen diameter.

Accordingly, there is a need for improved methods and devices for traversing a tubular body part.

SUMMARY OF THE INVENTION

Described herein are methods and devices for traversing a lumen, such as body lumen. Unlike traditional devices, the embodiments described herein use independently expandable and movable tubing elements to drive the device through a lumen. The tubing elements, in at least one embodiment, are adapted to reduce slippage. For example, the tubing elements can include a traction surface that facilitates gripping of the lumen walls.

In one embodiment, the device includes an elongate body extending from a proximal end to a distal end along a longitudinal axis. The distal end can include first and second tubing elements, each tubing element adapted for independent radial expansion. In addition to radial expansion, the tubing elements can move relative to one another. By sequentially expanding (and contracting) the tubing elements and moving the tubing elements relative to one another, the device can be driven through a lumen.

In one aspect, when the tubing elements are radially expanded to contact a lumen wall, they have the ability to grip an internal surface of a lumen without tearing the lumen. For example, the tubing elements can include a traction surface that helps to reduce slippage. In one embodiment, the tubing elements include a rough or porous coating that provides the traction surface.

Alternatively, or additionally, at least one of the tubing elements is formed from a mesh material that provides the traction surface. Longitudinally contracting (e.g., shortening the length of) the mesh tubing elements causes the tubing elements to radially expand and longitudinally expanding the tubing elements causes the tubing elements to radially contract.

The distal portion of the device can include first proximal and first distal body members mated with the first tubing element and second proximal and second distal body members mated with the second tubing element. To expand the first tubing element radially, the first proximal body member and the first distal body member can be brought together to shorten the length of the first tubing element. Similarly, to expand the second tubing element, the second proximal body member and the second distal body member can be brought together to shorten the length of the second tubing element. To reverse the process, the proximal and distal body members are moved apart to lengthen the tubing elements.

In another aspect, the device includes first and second control elements adapted to control expansion and contraction of the tubing elements. For example, proximally positioned control elements can allow a surgeon to remotely control expansion and contraction of distally positioned tubing elements. In addition, the control elements can be adapted to move the tubing elements relative to one another. For example, moving one of the control elements relative to the other control element can move one of the tubing elements relative to the other tubing element.

In another embodiment, a lumen traversing device is disclosed. The device includes at least two tubing elements movably positioned on an elongate body member and capable of selective and independent longitudinal movement. Each tubing element can have a selectively controllable length. For example, each tubing element can have a first configuration with an extended length and a contracted diameter and a second configuration with a reduced length and an expanded diameter. In one embodiment, the tubing elements are formed of a mesh material.

In yet another embodiment, a method of traversing a lumen is disclosed. The method can include the steps of providing a lumen traversing device having an elongate body extending from a proximal end to a distal end and including proximal and distal mesh tubing elements. In one aspect, the device is inserted into an internal lumen of a body and the proximal tubing element is expanded such that an outer surface of the expanded first tubing element sits against an inner surface of a body lumen. With the tubing elements expanded, the distal tubing element is moved distally relative to the proximal tubing element. The distal tubing element is then expanded such that an outer surface of the expanded distal tubing element sits against the inner surface of the lumen. With the distal tubing element expanded, the proximal tubing element is contracted and moved distally toward the distal tubing element.

In one aspect, the lumen traversing device including first and second proximally position control elements for independently controlling the proximal and distal tubing elements. For example, the first handle can be actuated to expand the proximal tubing element and the second handle can be actuated to expand the distal tubing element. In addition, the step of moving the proximal and/or distal tubing element distally can be performed by moving the first and/or second handle distally.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention The present invention generally provides methods and devices for traversing a lumen of a tubular body part, such as the GI tract. In an exemplary embodiment, the methods and devices utilize tubing elements to move the device through the lumen. The tubing elements can grip the lumen walls and push/pull against the walls to drive the device and/or hold the device in position relative to the lumen wall. A person skilled in the art will appreciate that methods and devices disclosed herein can have a variety of configurations, and that they can be adapted for use in a variety of medical procedures. For example, the methods and devices can be used for diagnostic purposes, such as for examining the intraluminal wall of a tubular body part, as a delivery means for delivering an implant, tool, air, water, light, energy, medications, radio-paque agents, etc, and/or to conduct an endoscopic surgical procedure at a remote site. While the invention is described herein primarily with respect to a GI tract, one skilled in the art will appreciate that the device of the invention can be used to access other lumens of the body.

Figures 1, 2:
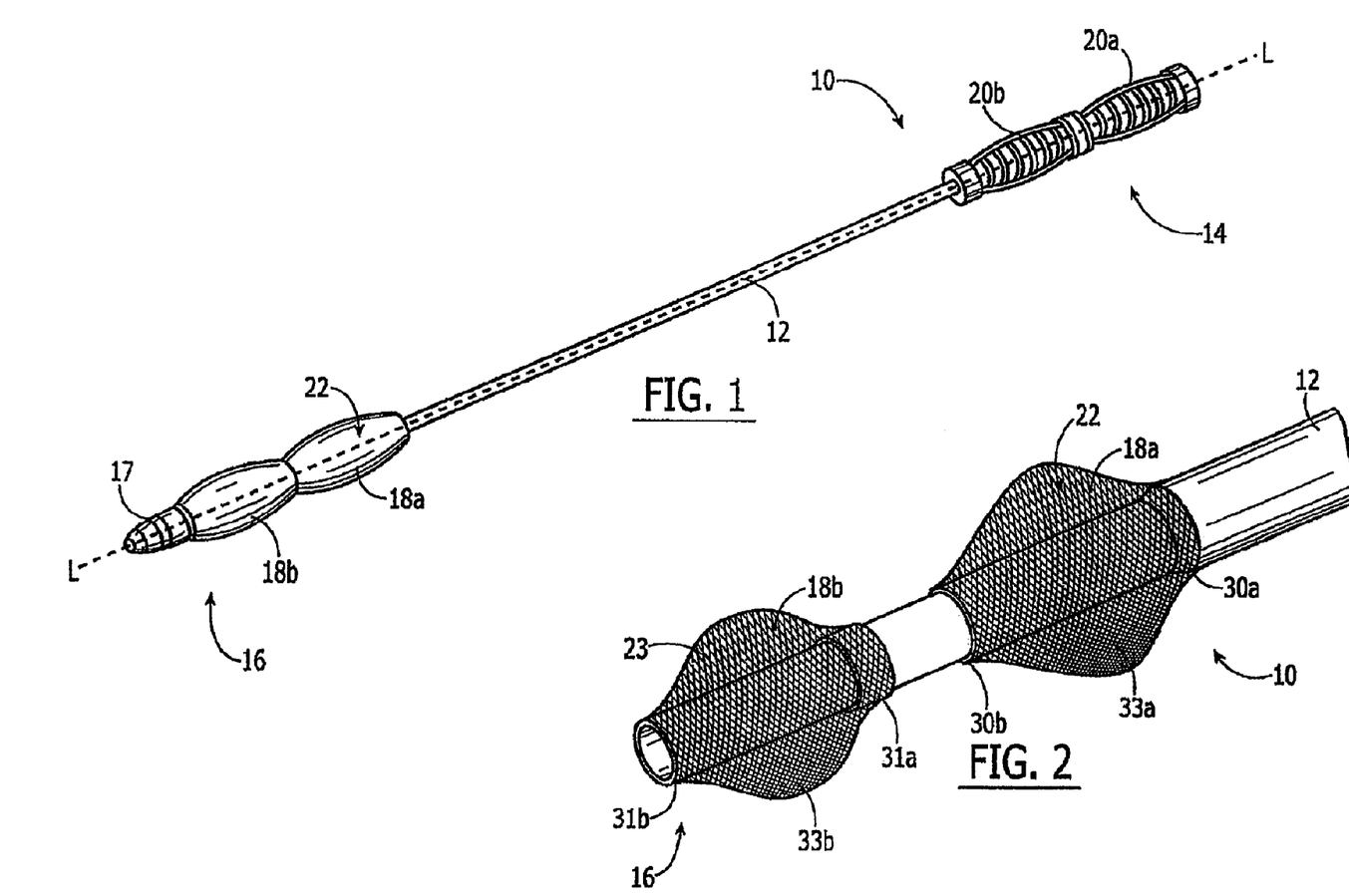
FIG. 1 is a perspective view of one embodiment of a lumen traversing device described herein.
FIG. 2 is a partial perspective view of a device described herein having tubing elements formed of a mesh material.

FIG. 1 illustrates one exemplary embodiment of device 10 including an elongate body 12 extending along a longitudinal axis L from a proximal end 14 to a distal end 16. In one aspect, the distal end 14 of device 10 includes a distal tip 17 that can have a conical shape to facilitate insertion and movement of the device through a lumen. In addition, or alternatively, distal tip 17 can be adapted to mate with a medical device and/or an implant for delivery to a treatment area. One skilled in the art will appreciate that distal tip 17 can have a variety of shapes and sizes depending on the intended use of device 10, including for example, delivery of gastrointestinal implants and surgical instruments.

The device 10 can include at least two selectively and independently expandable and contractible tubing elements 1 8a, 1 8b, which will sometimes be referred to herein as "balloons". In one aspect, tubing elements 18a, 18b are positioned at the distal end 14 of body 12 and can be actuated with proximally positioned control elements 20a, 20b. Manipulation of the control elements can, as described below, cause relative movement of the tubing elements 18a, 18b along axis L. In addition, control elements 20a, 20b can facilitate the selective expansion and contraction of the tubing elements 18a, 18b. Coordinated distal movement and radial expansion and contraction of the tubing elements 18a, 18b will enable the device 10 to effectively and conveniently navigate to remote regions of an internal body lumen.

Tubing elements 18a, 18b can be formed from a variety of materials which, when in a tubular form, are able to radially expand when the length of the tubular member is decreased and which are able to radially contract when the length of the tubular member is increased. Exemplary materials can include biocompatible polymers, metals, and metal alloys that are in the form of a woven mesh. An exemplary material is a woven mesh fabric formed from nylon fibers, nickel-titanium shape memory alloy ("Nitinol") wires, stainless steel wires (e.g., 300 series or 400 series), and combinations thereof.

In one aspect, the material from which the tubing elements 18a, 18b are formed assists the tubing elements with gripping the inner walls of a lumen. For example, the material can provide traction to the tubing elements in their expanded state, such that the tubing elements can hold their position against the lumen wall. In one embodiment, the balloons can include a friction-enhancing treatment or surface feature 22 to assist the balloons in gripping the lumen wall. Where the lumen wall is an anatomical surface, traction surface 22 is preferably adapted such that it grips the wall without tearing it. For example, traction surface 22 can be a porous or rough coating or overlayer which is positioned on the surface of balloons 18a, 18b. One skilled in the art will appreciate that a variety of materials can provide a gripping surface.

Alternatively, traction surface 22 can be provided by the outer surface of the tubular member itself. For example, balloons 18a and/or 18b can be formed from a woven mesh material as shown in FIG. 2. When pressed against a lumen wall, the surface of balloons 18a, 18b can provide a better hold than conventional devices that have a smooth surface. The woven mesh fabric possesses a rough and/or porous surface that provides traction surface 22, such that the balloons can adequately grip a lumen wall without tearing the lumen. In addition, the mesh material can provide pores or openings 23 that expand when the mesh is expanded and/or contract when the mesh is contracted. In the expanded state when the tubing elements are pressed against the inner wall of a lumen, openings 23 can facilitate gripping. Conversely, when the balloon is contracted, the contracted (or closed) openings 23 can more easily pass through the lumen.

One skilled in the art will appreciate that the term "mesh" is used to refer to the variety of materials having a porous surface including braided, woven, and web-like materials. In addition, "mesh" can include materials formed from a sheet having numerous apertures. In one aspect, the mesh balloons are woven from flexible or expandable wires. Such a mesh can be woven in a variety of patterns depending on the desired mesh density and the materials from which the mesh is formed. For example, the mesh can be woven in an under/over patterns with the wires of the mesh positioned at an angle with respect to the longitudinal axis L of the device. One skilled in the art will appreciate that the wires can be formed of individual strands composed of different materials, and/or that wires of different compositions can be used.

Regardless of the configuration of the tubing elements, they are preferably sized and shaped according to the desired use. For example, the tubing elements in their radially contracted state, together with body 12 should be sized to fit through an opening in the body that will be used to gain access to the lumen. Preferably, the opening in the body is a natural orifice. In addition to being sized to fit through an opening in the body, the device, including the balloons in their radially contracted state must also be sized to fit through the narrowest portion of the lumen through which the device is intended to traverse. Further, the tubing elements should have dimensions in their radially expanded state such that they are able to contact the widest portions of the lumen wall through which the device will be passed.

Tubing elements 18a, 18b in one embodiment have a generally elongate or tubular shape that extends from a proximal end 30a, 31a to a distal end 30b, 31b. Radial expansion of tubing elements 18a, 18b can be achieved by moving the proximal end 30a, 31a and distal end 30b, 31b together. When the ends are brought together, the length of the balloon decreases and the middle portion 33a, 33b of balloons 18a, 18b radially expands. Conversely, moving the proximal end 30a, 31a and distal end 30b, 31b apart will increase the length of the balloons, thereby contracting the diameter of the balloons.

Figure 3:
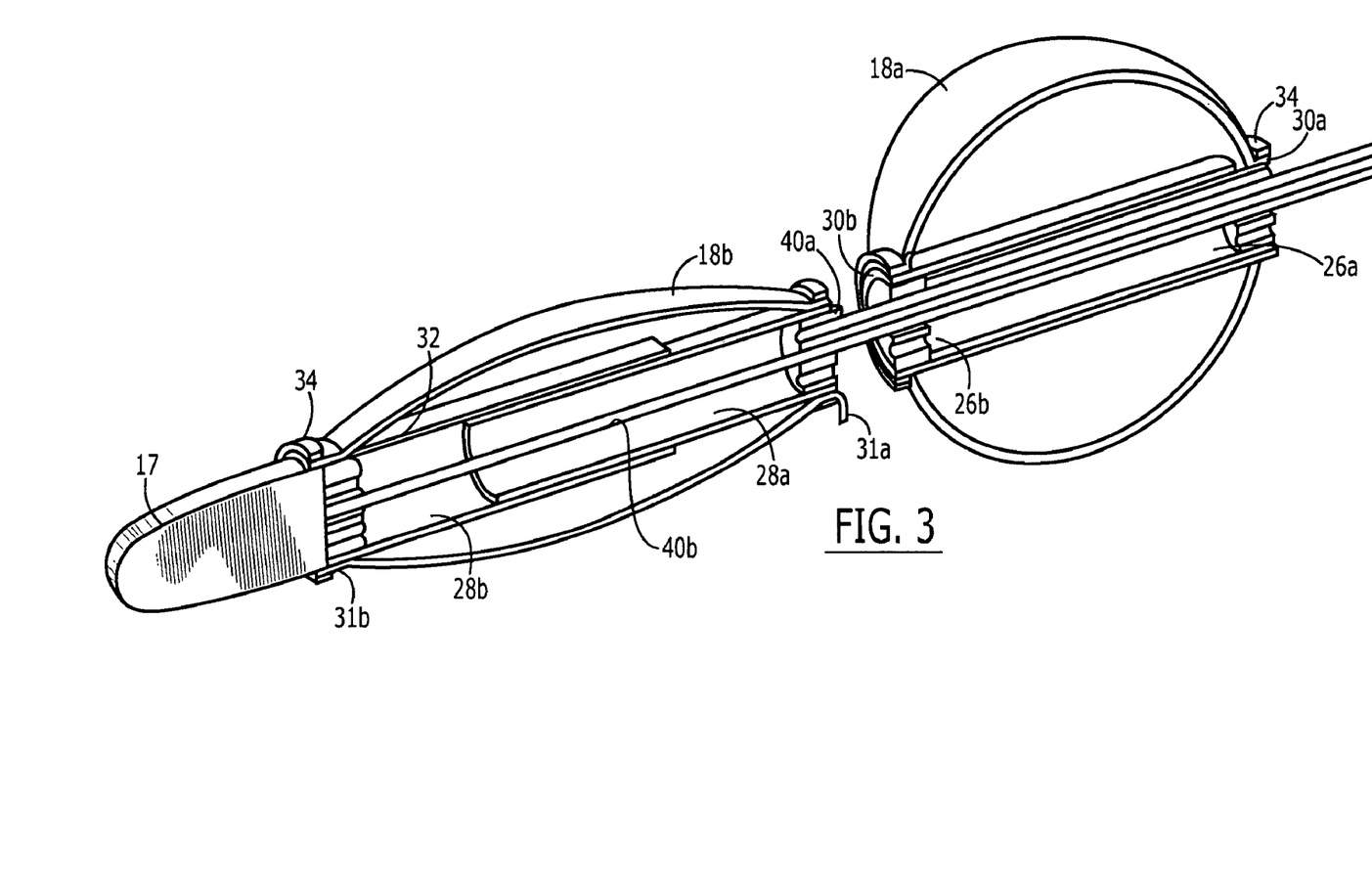
FIG. 3 is a cut-away view of the distal portion an embodiment of the device described herein.

In one embodiment, expansion and contraction of the tubing elements 18a, 18b can be achieved by relative movement of the body members 26a, 26b, 28a, 28b. FIG. 3 illustrates one embodiment of the distal portion of device 10 with balloons 18a, 18b mated to body members 26a, 26b, 28a, 28b. In particular, balloon 18a is mated at ends 30a, 30b to first proximal and first distal body members 26a, 26b, respectively, and balloon 18b is mated at ends 31a, 31b to second proximal and second distal body members 28a, 28b, respectively. Actuation of proximal control elements 20a, 20b can move the proximal and distal body members relative to one another and cause the length of the balloons to decrease (i.e., by bringing the proximal body member 26a, 28a and distal body member 28a, 28b together), thereby radially expanding the balloons. Conversely, actuation of the control elements to increase the length of the balloons (i.e., by moving the proximal body member 26a, 28a and the distal body member 28a, 28b apart) will cause the diameter of the balloon 18a, 18b to contract. In addition to controlling the contraction and expansion of balloons 18a, 18b, actuation of control elements 20a, 20b will enable the body members 26a, 26b, 28a, 28b to move the balloons 18a, 18b relative to one another, independently, along longitudinal axis L. For example, first body members 26a, 26b and second body members 28a, 28b can be moved longitudinally relative to one another.

Tubing elements 18a, 18b can be mated with body members 26a, 26b, 28a, 28b by a variety fixation techniques. For example, as shown in FIG. 3, tubing elements 18a, 18b can be fixed between an outer surface 32 of the body member and a retention band 34. One skilled in the art will appreciate that tubing elements 18a, 18b can be fixed to body members 26a, 26b, 28a, 28b by a variety of other alternative or additional fixation methods. For example, the balloons can be bonded, welded, adhered, and/or mated with a friction fit to body 12.

In one embodiment, actuating rods 40 that extend from control elements 20a, 20b to body members 26a, 26b, 28a, 28b can be used to move body members 26a, 26b, 28a, 28b and control the selective expansion, contraction and longitudinal movement of balloons 18a, 18b. In one embodiment, illustrated in FIG. 3, multiple rods are used. For example, rod 40b can extend to the second distal body member 28b, while rod 40a can extend to second proximal body member 28a. Rods 40a, 40b can be mated with the second body members 28a, 28b such that moving rods 40a, 40b will result in corresponding movement of the body members. In addition, rods 40a, 40b can be moved together to move balloons 18b relative to balloons 18a. Similarly, with respect to balloons 18a, body members 26a, 26b can mate with two additional rods (not shown) to allow control of balloons 18a. The rods can control radial expansion of balloon 18a as well as relative movement of balloons 18a with respect to 18b. For example the rods can move balloon 18a proximally and distally relative to balloon 18b.

While expansion and contraction of tubing elements 18a, 18b and body members 26a, 26b, 28a, 28b is described with respect to rods, one skilled in the art will appreciate that the balloons can be controlled in a variety of alternative ways. For example, one skilled in the art will appreciate that a variety of other mechanical actuation elements can be used to selectively control the length of each tubing element, and hence expansion/contraction, and the independent longitudinal movement of each tubing element.

Body 12 of device 10 between tubing elements 18a, 18b and control elements 20a, 20b, in one embodiment, can be defined by the rods as discussed above. In another embodiment, body 12 includes an outer protective shell defining an inner lumen (not shown) and rods 40a, 40b can be disposed therein. The outer shell can also be adapted to contain various components therein and/or can be adapted for the delivery of tools and/or therapeutics. In one exemplary, body 12 can include a passageway for delivering implants, tools, and/or treatment media from the proximal portion 14 to the distal portion 16 of device 10

The elongate body 12 (e.g., rods 40 and/or the outer shell) can be formed from a variety of materials, including materials that provide flexibility and/or deformability. In certain exemplary embodiments, the elongate body 12 is formed from a metal, a metal alloy, biocompatible polymer, or combinations thereof. For example, the rods may be formed from braided stainless steel sheathed in a polymer overtube (e.g., polyethylene, polypropylene, and/or nylon). The rods may also be made of solid flexible materials such as Nitinol or Spring steel. A person skilled in the art will appreciate that the materials used to form body 12 can be selected based on the intended use of the device and the need for the device to maneuver around anatomical features.

Figure 4:
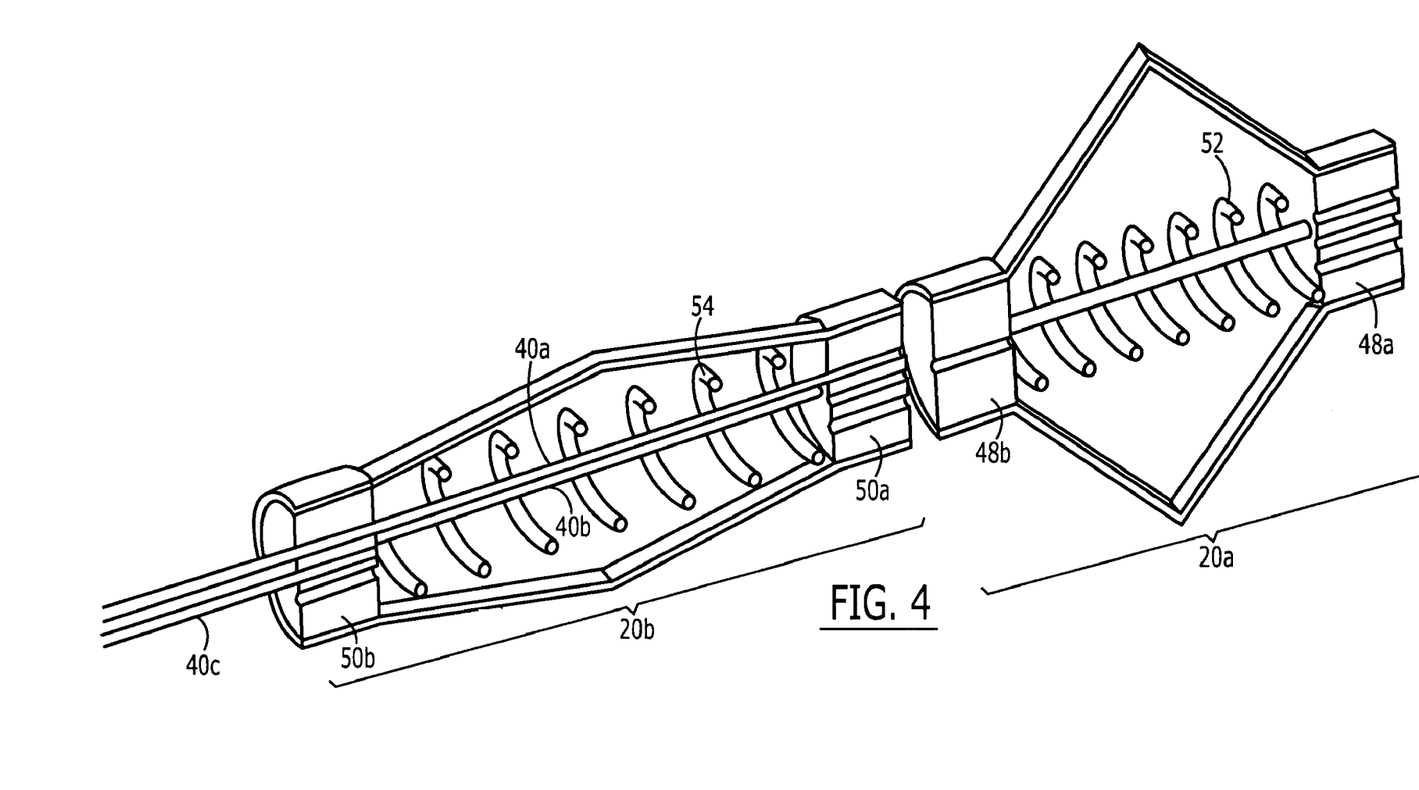
FIG. 4 is a cut-away view of the proximal portion of an embodiment of the device described herein.

The proximal portion of elongate body 12 can extend to a mechanism for controlling the expansion/contraction and/or relative movement of tubing elements. FIG. 4 illustrates a partial cut-away view of one embodiment of the proximal end of device 10 including first and second control elements 20a, 20b that allow a user to control the movement of the proximal and distal tubing elements 18a, 18b (not illustrated in FIG. 4). Each control element 20a, 20b can control one of tubing elements 18a, 18b.

In one aspect, control elements 20a, 20b each include a proximal and a distal control member that are moved relative to one another to control the diameter of tubing elements 18a, 18b. As shown, in FIG. 4, control elements members 48a, 48b, 50a, 50b can mate with rods 40a, 40b, 40c (for the sake of clarity, only three rods are shown). Actuating handle 20b moves second proximal and distal handle members 50a, 50b relative to one another, causing rods 40a, 40b to move relative to one another. Movement of rods 40a, 40b causes balloon 18b to expand/contract as discussed above. Similarly, actuating handle 20a moves second proximal and distal control elements member 48a, 48b toward (or away) from one another, causing the diameter of balloon 18a to expanded (or contract).

In addition, moving control elements 20a, 20b relative to one another can move tubing elements 18a, 18b relative to one another. For example, control elements 20a, 20b can be moved toward and away from each other, thereby moving the rods associated with the control elements. Since the rods connect the balloons 18a, 18b to the control elements 20a, 20b, relative movement of control elements 20a, 20b moves tubing elements 18a, 18b relative to one another. For example, moving control elements 20a, 20b away from each other moves tubing elements 18a, 18b away from each other, and conversely, moving control elements 20a, 20b toward one another moves tubing elements 18a, 18b toward one another.

As shown in FIG. 4, control elements 20a, 20b can include springs 52, 54 that bias the balloons to an expanded configuration. When tubing elements 18a, 18b are positioned within a lumen and the control elements 20a, 20b are not actuated, springs 52, 54 hold device 10 in position relative to the lumen by the action of the expanded tubing elements against the lumen wall. Squeezing one or both control elements 20a, 20b against the force of the spring causes the tubing element(s) to contract such that one or both of tubing elements 18a, 18b can be moved through the lumen.

Figure 5:
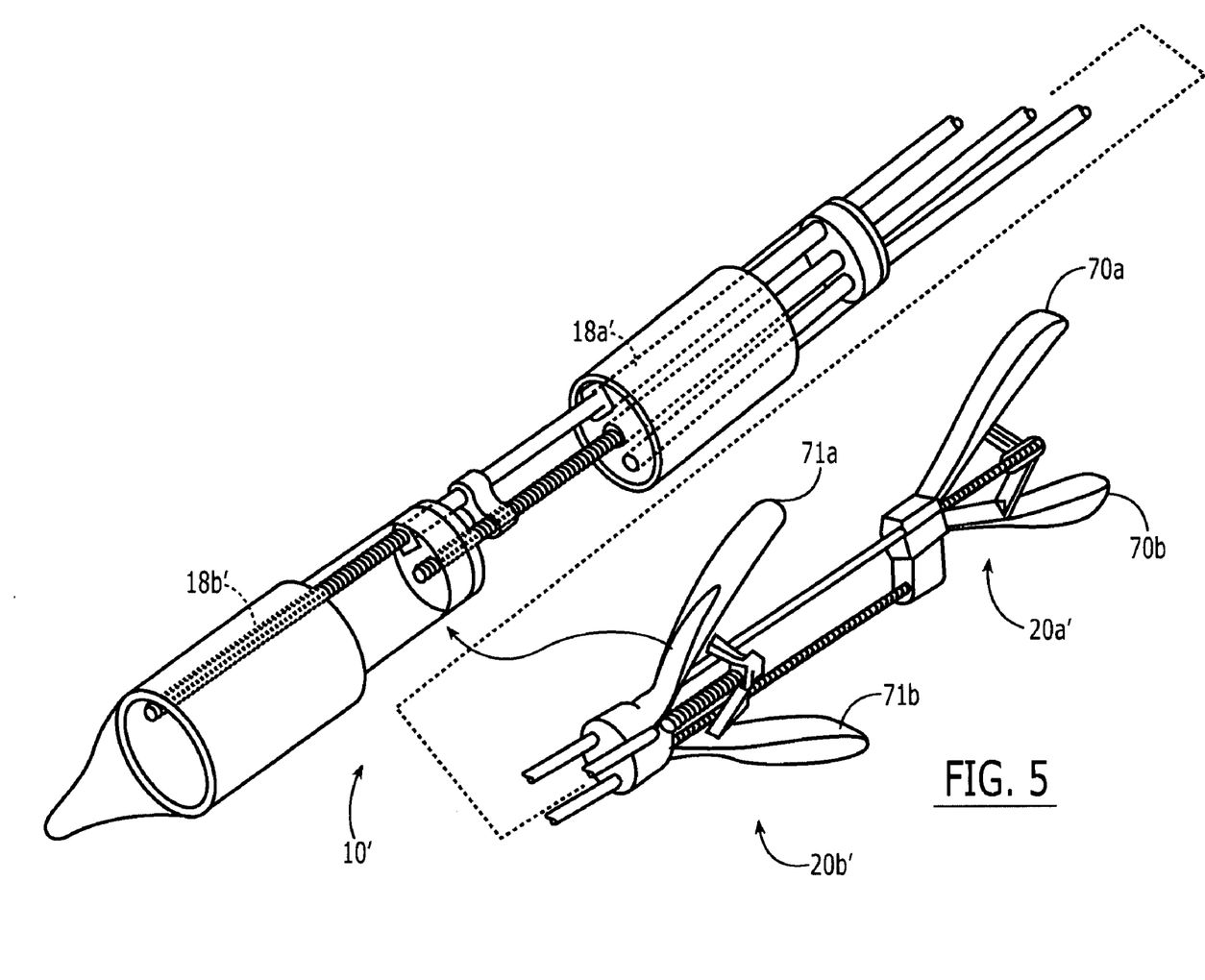
FIG. 5 is a perspective view of another embodiment of a device described herein.

FIG. 5 illustrates an alternative embodiment of device 10' that includes control elements 20a', 20b' connected to tubing elements 18a', 18b'. Each control element 20a', 20b' includes first and second lever arms 70a, 70b, 71a, 71b. Moving the lever arms together or apart controls rods 40 and thus tubing elements 18a', 18b'. One skilled in the art will appreciate that a variety of alternative control elements can be used with device 10 depending on the intended use and the configuration of the tubing elements 18a, 18b.

Figure 6:
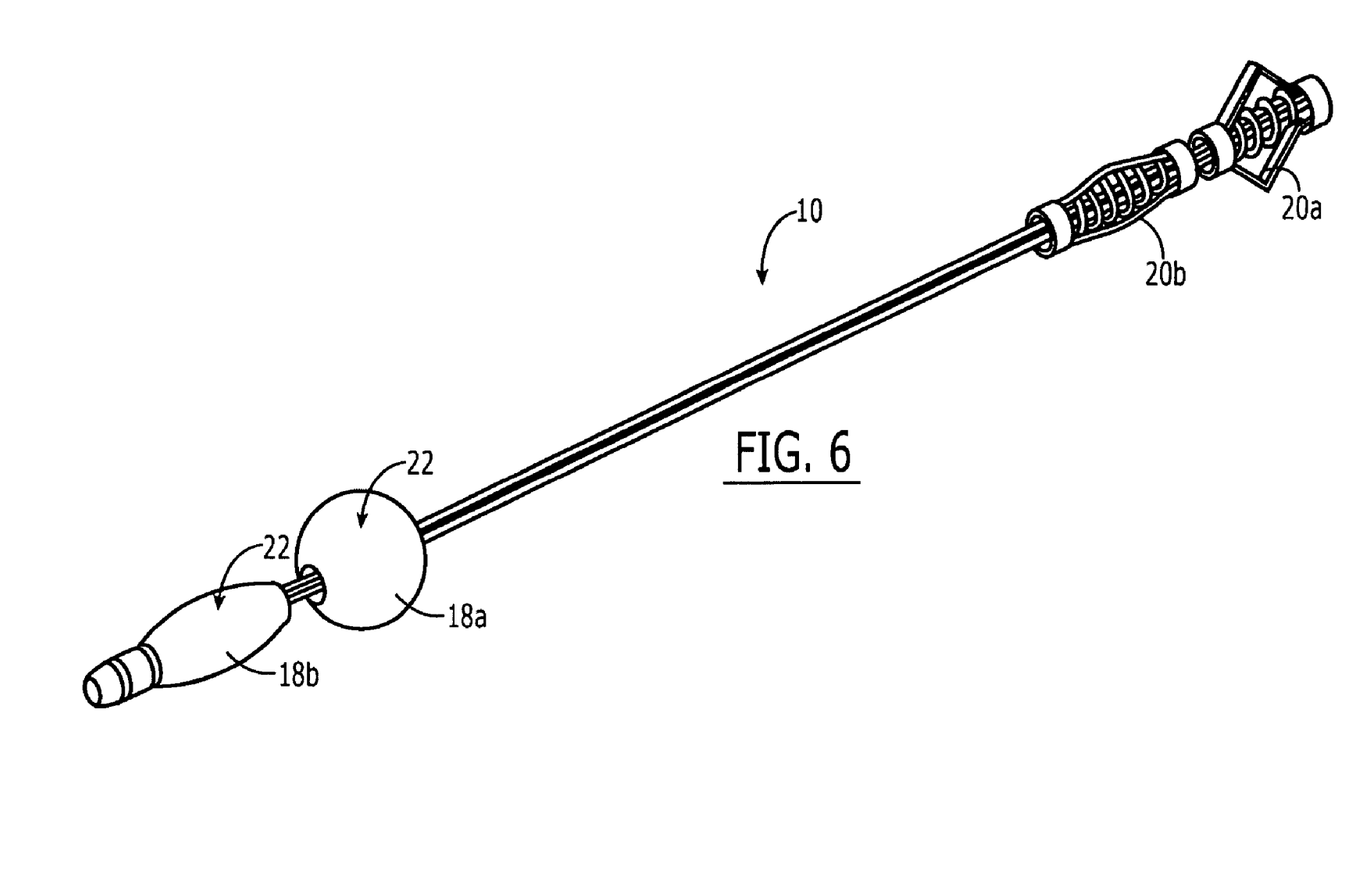
FIG. 6 is a perspective view of one embodiment of a device described herein with a proximal tubing element in the expanded position.
Figure 7:
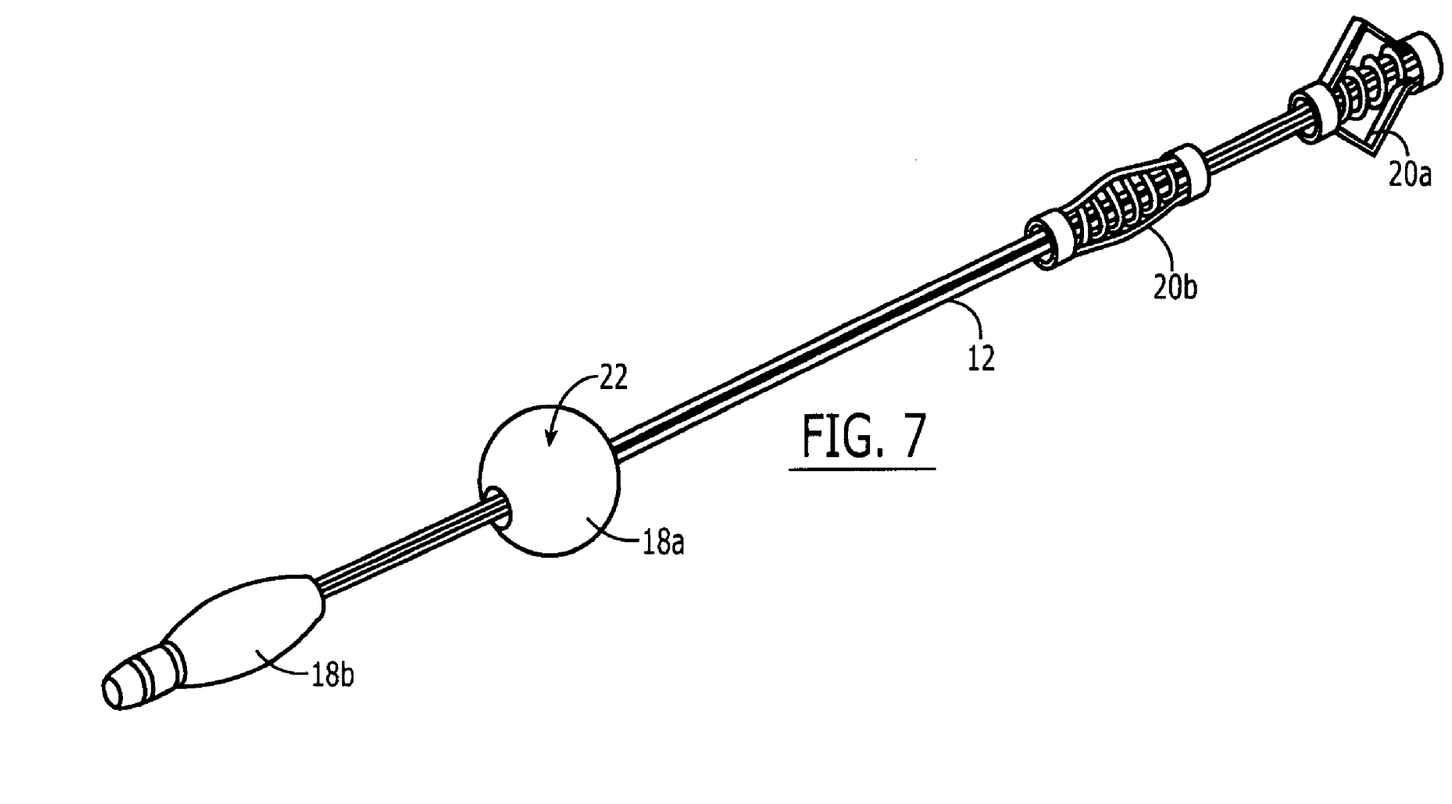
FIG. 7 is a perspective view of the device of FIG. 6 with the distal tubing element moved distally.
Figure 8:
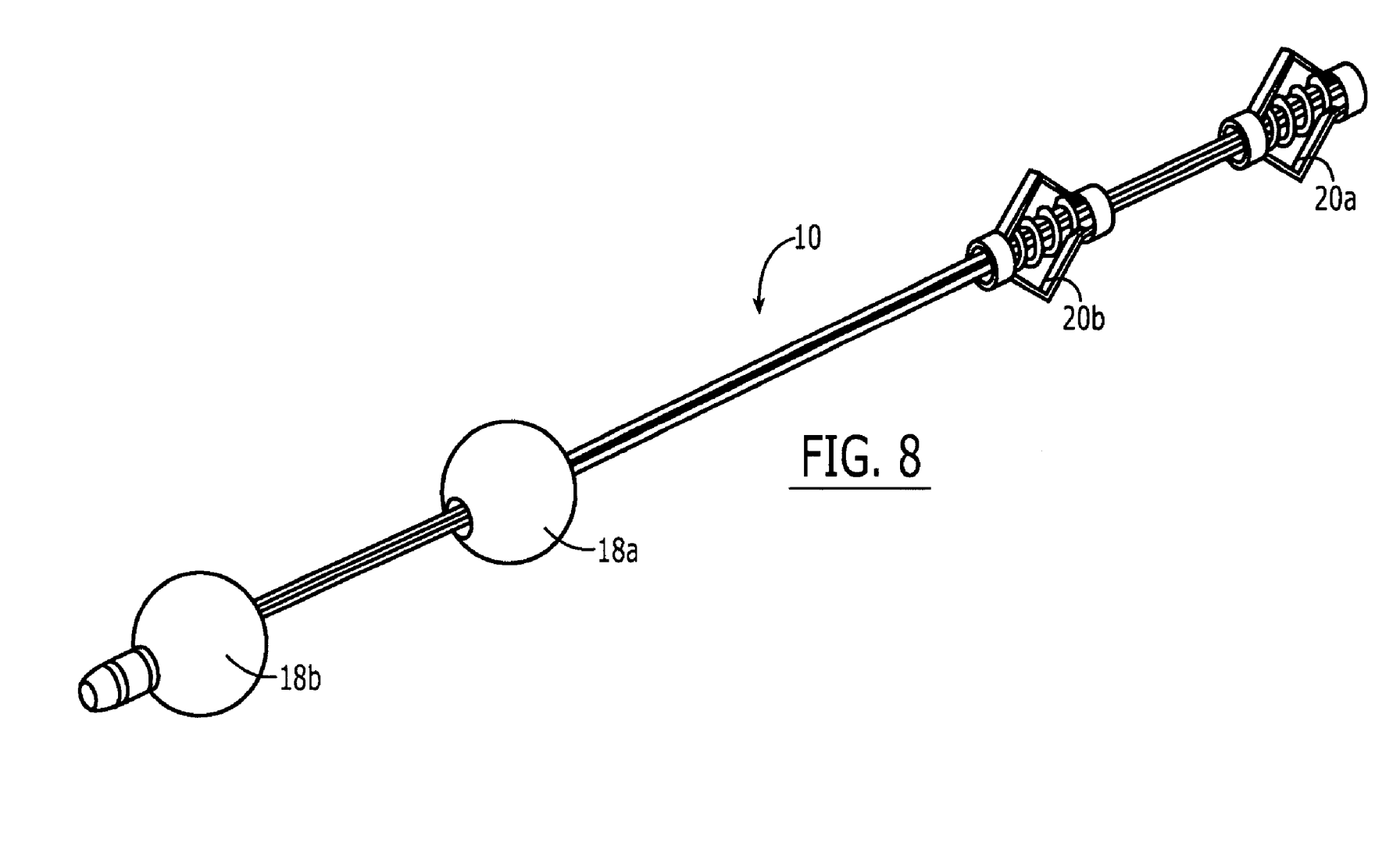
FIG. 8 is a perspective view of the device of FIG. 7 with the proximal and distal tubing elements in the expanded position.
Figure 9:
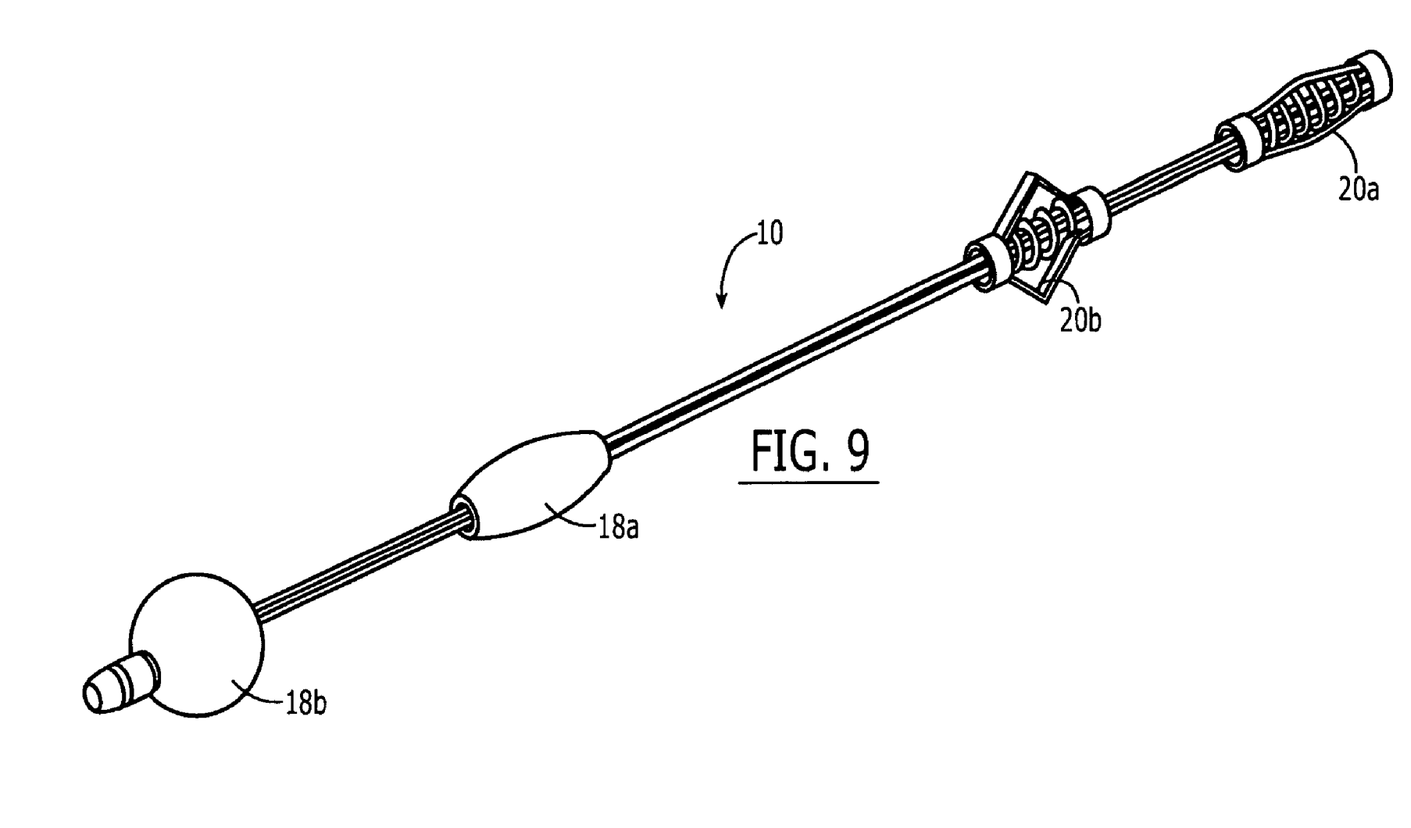
FIG. 9 is a perspective view of the device of FIG. 8 with the proximal tubing element in the contracted position.
Figure 10:
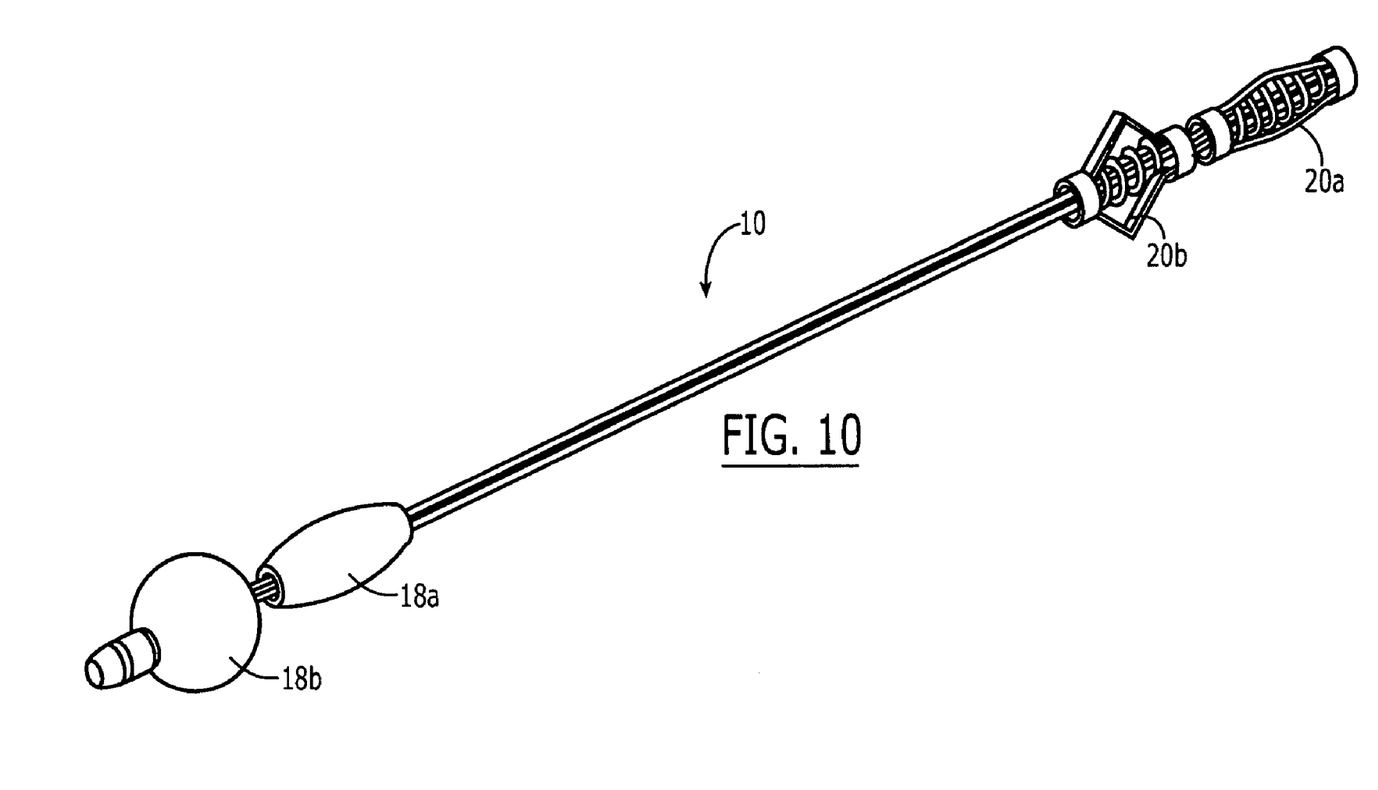
FIG. 10 is a perspective view of the device of FIG. 9 with the proximal tubing element moved distally.

FIGS. 6 through 10 illustrate one embodiment of a method for moving at least a portion of device 10 (e.g., the distal portion) through a body lumen (not shown). Following preparation of the patient for surgery, the device is inserted into the patient's body through an orifice, such as the anus. Next, as shown in FIG. 6, the length of proximal balloon 18a is decreased so that it radially expands to contact an inner surface of a lumen. As shown in FIG. 7, distal balloon 18b, which is in a lengthened, contracted diameter condition, is then moved distally through the lumen while the expanded proximal balloon 18a anchors the device in position relative to the lumen wall. As noted above, the surface 22 of balloon 18a helps to prevent/reduce slippage of the device. As shown in FIG. 8, once balloon 18b is moved into its desired position, the length of balloon 18b is decreased to expand the balloon to contact the lumen wall and hold its position. The length of proximal balloon 18a can then be decreased to contract the balloon, and balloon 18a is then moved distally toward balloon 18b as shown in FIGS. 9 and 10, while the expanded balloon 18b holds device 10 within lumen. This procedure is repeated to advance the device to a desired location within the lumen.

A person skilled in the art will appreciate that, while the various figures describe and illustrate a device 10 having two tubing elements 18a, 18b, the device 10 can include any number of tubing elements to facilitate movement of the device through a lumen.

In certain exemplary embodiments, device 10 can be used to examine and/or treat the GI tract. Since the size of the device 10 can be relatively small, and since the tubing elements 18a, 18b can be selectively reduced in diameter, the device can be inserted deeper than standard endoscopes and other intraluminal devices. For the upper GI, the device can be inserted through a patient's mouth, and for the lower GI the device can be inserted through the patient's anus. Regardless, device 10 preferably has a size that allows the device to engage the walls of and move through the GI tract. Typically, the maximum diameter of the GI tract is about 30 mm in the lower GI, and about 16 mm in the upper GI. Accordingly, in certain exemplary embodiments tubing elements 18a, 18b can have a diameter that ranges from about 16 mm in the unexpanded condition to about 33 mm in the expanded condition. The shape and size can, of course, vary depending on the intended use.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of traversing an internal lumen of a body, comprising:
    a. inserting a lumen traversing device having an elongate body extending from a proximal end to a distal end and including immediately adjacent distal and proximal mesh tubing elements;
    b. moving at least one proximal actuating rod to radially expand the proximal tubing element such that a length of the proximal tubing element decreases, wherein an outer surface of the expanded proximal tubing element engages an inner surface of the lumen;
    c. moving at least one distal actuating rod to radially contract the distal tubing element such that a length of the distal tubing element increases, and moving proximal and distal ends of the radially-contracted distal tubing element distally away from the immediately adjacent proximal tubing element;
    d. moving the at least one distal actuating rod to radially expand the distal tubing element such that a length of the distal tubing element decreases, wherein an outer surface of the expanded distal tubing element engages the inner surface of the lumen;
    e. moving the at least one proximal actuating rod to radially contract the proximal tubing element such that a length of the proximal tubing element increases, and moving proximal and distal ends of the radially-contracted proximal tubing element distally toward the distal tubing element; and
    f. repeating steps b-e until the device reaches a desired site within the lumen.

2. The method of claim 1, wherein the device includes a medical device effective for use in a surgical and/or diagnostic procedure.

3. The method of claim 2, wherein the medical device is an endoscope.

4. The method of claim 1, wherein inserting the lumen traversing device comprises inserting the lumen traversing device into natural orifice in a body.

5. The method of claim 1, wherein the outer surface of the proximal tubing element comprises a plurality of openings formed therein, and wherein the plurality of openings expand when the proximal tubing element radially expands and contract when the proximal tubing element radially contracts.

6. The method of claim 1, wherein the outer surface of the distal tubing element comprises a plurality of openings formed therein, and wherein the plurality of openings expand when the distal tubing element radially expands and contract when the distal tubing element radially contracts.

7. A method of traversing an internal lumen of a body, comprising:
    inserting an elongate body having immediately adjacent proximal and distal mesh tubing elements into a body lumen;

moving at least one proximal actuating rod to move the proximal tubing element from a first radially-contracted and axially-expanded configuration to a second radially-expanded and axially-contracted configuration, wherein the outer surface of the proximal tubing element engages an inner surface of the lumen;

moving at least one distal actuating rod to move proximal and distal ends of the distal tubing element distally away from a distal end of the immediately adjacent proximal tubing element, the distal tubing element being in a first radially-contracted and axially-expanded configuration;

moving the at least one distal actuating rod to move the distal tubing element from the first radially-contracted and axially-expanded configuration to a second radially-expanded and axially-contracted configuration, wherein the outer surface of the distal tubing element engages an inner surface of the lumen;

moving the at least one proximal actuating rod to move the proximal tubing element from the second radially-expanded and axially-contracted configuration to the first radially-contracted and axially-expanded configuration; and moving the at least one proximal actuating rod to move proximal and distal ends of the proximal tubing element distally toward the proximal end of the distal tubing element.

8. The method of claim 7, wherein moving the proximal tubing element from the first configuration to the second configuration comprises moving the proximal and distal ends of the proximal tubing element towards each other.

9. The method of claim 7, wherein moving the proximal tubing element from the second configuration to the first configuration comprises moving the proximal and distal ends of the proximal tubing element away from each other.

10. The method of claim 7, wherein moving the distal tubing element from the first configuration to the second configuration comprises moving the proximal and distal ends of the distal tubing element towards each other.

11. The method of claim 7, wherein moving the distal tubing element from the second configuration to the first configuration comprises moving the proximal and distal ends of the distal tubing element away from each other.

12. The method of claim 7, wherein the at least one proximal actuating rod comprises a first actuating rod coupled to the proximal end of the proximal tubing element and a second actuating rod coupled to the distal end of the proximal tubing element, and wherein moving the proximal tubing element between the first and second configurations comprises moving the first and second actuating rods relative to each other.

13. The method of claim 12, wherein the at least one distal actuating rod comprises a third actuating rod couple to the proximal end of the distal tubing element is and a fourth actuating rod coupled to the distal end of the distal tubing element, and wherein moving the distal tubing element between the first and second configurations comprises moving the third and fourth actuating rods relative to each other.

14. The method of claim 13, wherein moving the proximal and distal tubing elements relative to one another comprises moving the first and second actuating rods relative to the third and fourth actuating rods.

15. A method for traversing a body lumen, comprising:

moving first and second actuating rods relative to one another to radially-expand a first mesh tubing element disposed on an elongate member to cause the first mesh tubing element to engage an inner wall of a body lumen containing the elongate member;

moving third and fourth actuating rods relative to one another to radially-contract a second mesh tubing element disposed on the elongate member to cause the second mesh tubing element to release an inner wall of the body lumen containing the elongate member;

moving the third and fourth actuating rods relative to the first and second actuating rods to move the second mesh tubing away from the first mesh tubing element;

moving the third and fourth actuating rods relative to one another to radially-expand the second mesh tubing element to cause the second mesh tubing element to engage an inner wall of the body lumen;

moving the first and second actuating rods relative to one another to radially-contract the first mesh tubing element to cause the first mesh tubing element to release the inner wall of the body lumen; and moving the first and second actuating rods relative to the third and fourth actuating rods to move the first mesh tubing element toward the second mesh tubing element.

* * * * *